United States Patent [19]

Brown

[11] 4,203,979
[45] May 20, 1980

[54] INSECTICIDAL 1-SEC. AND TERT.-ALKYL-2-DISUBSTITUTED-PHOSPHORYL HYDRAZINES

[75] Inventor: Michael J. Brown, Randolph, N.J.

[73] Assignee: GAF Corporation, New York, N.Y.

[21] Appl. No.: 3,959

[22] Filed: Jan. 16, 1979

[51] Int. Cl.$^2$ ............................. A01N 9/36; C07F 9/24
[52] U.S. Cl. ................................. 424/220; 260/551 P; 260/923
[58] Field of Search ............................. 260/923, 551 P; 424/211, 220

[56] References Cited

U.S. PATENT DOCUMENTS

| | | | |
|---|---|---|---|
| 2,855,423 | 10/1958 | Blair | 260/923 |
| 2,906,770 | 9/1959 | Debo | 260/923 |

FOREIGN PATENT DOCUMENTS 626632  8/1961  Canada ....................................... 260/923

*Primary Examiner*—Anton H. Sutto
*Attorney, Agent, or Firm*—Walter C. Kehm; Walter Katz

[57] ABSTRACT

Compounds of the formula:

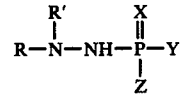

where
  R is a secondary or tertiaryalkyl, $C_4$–$C_{10}$,
  R' is hydrogen, alkyl, $C_1$–$C_6$ or acyl, $C_2$–$C_6$,
  X is oxygen or sulfur, and,
  Y and Z are independently alkyl, alkenyl, alkoxy, thioalkoxy, alkenyloxy or thioalkenyloxy, $C_1$–$C_6$,
are described herein.

These compounds are useful as insecticides or miticides.

18 Claims, No Drawings

INSECTICIDAL 1-SEC. AND TERT.-ALKYL-2-DISUBSTITUTED-PHOSPHORYL HYDRAZINES

BACKGROUND OF THE DISCLOSURE

1. Field of the Invention

This invention relates to novel 1-sec. or tert.-alkyl-2-disubstituted phosphoryl hydrazine compounds which are useful as insecticides or miticides.

2. Description of the Prior Art

Compounds in the substituted phosphoryl hydrazine series have been reported in the literature. For example, the articles referred to in Chemical Abstracts 55,9320g; 54,7051f; 52,4920a; 50,2415h and 53,3113; and in U.S. Pat. No. 2,906,770 and German Pat. No. 1,011,432, there are disclosed related hydrazine compounds and their synthesis. However, none of these prior art compounds have the essential structural features of the novel compounds of this invention, which, significantly, provide useful agricultural insecticidal and miticidal activity.

SUMMARY OF THE INVENTION

What is described herein are novel compounds of the formula:

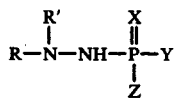

where
R is a secondary or tertiary alkyl, $C_4$-$C_{10}$,
R' is hydrogen, alkyl, $C_1$-$C_6$, or acyl $C_2$-$C_6$,
X is oxygen or sulfur, and,
Y and Z are independently alkyl, $C_1$-$C_6$, alkenyl, $C_2$-$C_6$, alkoxy, $C_1$-$C_6$, thioalkoxy, $C_1$-$C_6$, alkenyloxy, $C_2$-$C_6$ or thioalkenyleoxy, $C_2$-$C_6$.

These novel compounds exhibit useful insecticidal and miticidal activity.

In the preferred form of the invention, R is a tertiary alkyl group; R' is hydrogen; X is oxygen or sulfur; and Y and Z are both alkoxy.

DESCRIPTION OF THE INVENTION

The novel compounds of the invention may be prepared by reaction between a suitably branched alkyl hydrazine and a dialkylphosphite, using the solid-liquid phase transfer catalysis technique described by Zwierzak and Sulewska in Synthesis (1976), p. 835 for related compounds. The starting dialkylphosphite material usually is available commercially, e.g. from the Aldrich Chemical Co., or can be made by the method given in Chemical Abstracts 55,14308d. The products of the reaction are the desired 1-sec. or tert.-alkyl-2-dialkoxy phosphoryl hydrazines.

Alternatively, the compounds herein may be synthesized by reaction between a sec. or tert-alkyl hydrazine and an alkylalkoxychlorophosphate under classical homogeneous solution conditions, in the presence of an organic base, as described by Pelchowicz in the J. Chem. Soc. (1961), p. 238, for related compounds. The alkylalkoxychlorophosphate also is available commercially, or can be made by reaction of a trialkylphosphite with an appropriate alkyl halide to give a dialkoxyalkyl-phosphonate, which may be chlorinated with oxalyl chloride to provide the desired starting material.

Either of the two methods will produce the 1-sec. or tert.-alkyl-2-disubstituted-phosphoryl hydrazine compounds of the invention, having the formula given above.

The 1-sec. or tert.-alkyl hydrazine starting material may be used in the form of its hydrochloride salt or as the free base in the phase transfer catalysis method while under homogeneous solution conditions only the free base is used. The chloro derivative of the dialkylphosphite also may be used in the phase transfer technique instead of the dialkylphosphite, and, is probably formed "in situ" during the catalyzed reaction. The corresponding thiophosphite and chlorothiophosphate compounds are used as starting materials where the thiophosphoryl hydrazines are the desired products.

Compounds in which R' is a substituent other than hydrogen, i.e. alkyl or acyl, are made by conventional alkylation or acylation of the parent compound, in which R' is hydrogen.

The preferred compounds of the invention are those in which R is a tertiary alkyl group, $C_4$-$C_6$, e.g. t-butyl, t-amyl, etc.; R' is hydrogen; X is oxygen or sulfur; and Y and Z are both lower alkoxy, e.g. methoxy or ethoxy.

The compounds in which R' is alkyl or acyl also are quite active insecticides but require additional synthetic steps to be prepared from the parent compounds.

As stated above, the invention compounds of the formula are useful as insecticides or miticides, and are most conveniently used as such when formulated into compositions. In another aspect, therefore, the invention provides insecticidal and miticidal compositions which comprise as an active ingredient compound of the formula in association with agriculturally and horticulturally acceptable diluent or carrier materials.

In this aspect of the invention the active ingredient is selected from among the specifically named compounds of the invention set out hereinabove.

The compositions are for use in agriculture or horticulture but the type of composition used in any instance will depend upon the particular purpose for which it is to be used.

In use, the invention compounds or compositions may be used to combat insects or mites in a variety of ways. Thus the insects themselves, or the locus of the insects or the habitat of the insects is treated with a compound or a composition according to the invention.

The invention also provides a method of treating plants to render them less susceptible to damage by insects, which comprises treating the plants, or the seeds, corms, bulbs, tubers, rhizomes or other propagative parts of the plants, or the medium in which the plants are growing with a compound or composition according to the invention.

The composition of the present invention may be applied to the soil of the insect susceptible plants on the site at a rate of about 1 pound or less to about 25 pounds per acre, or as a foliar dust or spray at concentrations of about 31 to 260 ppm, depending on various circumstances of the susceptibility of the insects, the weather, the stage of growth and various other factors. As a dust, it is more practical to extend it with diluents such as bentonite, chalk, clay, diatomaceous earth, fullers earth, mica, ground slate or any of the other usual carriers for agricultural chemicals. As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the insect.

Following are examples of preparation of the compounds of the invention, and are presented by way of illustration and are not intended to be limiting unless otherwise specified.

EXAMPLE 1

1-t-Butyl-2-Dimethoxyphosphoryl Hydrazine

A mixture of t-butylhydrazine hydrochloride (12.46 g, 0.1 mole), potassium carbonate (27.64 g, 0.2 mole) and triethylbenzyl ammonium chloride (0.3 g, 0.0013 mole) was stirred vigorously at reflux with dichloromethane (100 ml) and carbon tetrachloride (60 ml) for 30 minutes. A solution of dimethylphosphite (11.0 g, 0.1 mole) in dichloromethane (20 ml) was then added dropwise to this refluxing mixture and the mixture stirred and refluxed for an additional 20 hours. The mixture was then filtered and the filtrate dried over anhydrous magnesium sulfate. The dried filtrate, then was evaporated down to a viscous oil which was subjected to high vacuum for 2 or 3 hours to yield 14.5 g of a solid product, m.pt. 61°-8° C.

EXAMPLE 2

1-t Butyl-2-Dimethoxythiophosphoryl Hydrazine 1-t-Butyl-2-dimethoxythiophosphoryl hydrazine was synthesized in a similar manner to the method of Example 1, but with the substitution of dimethylchlorothiophosphate for the dimethylphosphite used in Example 1. A yellow solid was obtained, m.pt. 51°-4° C.

EXAMPLE 3

1-t-Butyl-2-Ethoxymethylphosphonyl Hydrazine

A solution of ethyl methylphosphonochloridate (14.25 g, 0.1 mole) in anhydrous ether (20 ml) was added dropwise with stirring to a mixture of t-butylhydrazine (8.82 g, 0.1 mole), triethylamine (18 ml, 0.3 mole) and ether (200 ml) at 0°-5° C. The mixture was then allowed to warm up to room temperature and left stirring overnight. Water was then added and the ethereal mixture removed. The aqueous phase was extracted twice with ether and the combined ether layers dried over magnesium sulfate and then evaporated down to give a viscous oil which solidified after removing other volatiles on a high vacuum line. The yield was 8.5 g, m.pt. 68°-70° C.

EXAMPLE 4

1-t-Butyl-1-Methyl-2-Dimethoxythiophosphoryl Hydrazine 1-t-Butyl-2-dimethoxythiophosphoryl hydrazine (11 g), potassium carbonate (4.4 g), methyliodide (10 ml.) and triethylbenzylammonium chloride (0.3 g) were added to methylene dichloride (15 ml.) and the mixture was refluxed for 4 hrs. After cooling, filtered mixture was fitted and the organic filtrates were evaporated to dryness. The residue was crystallized from a chloroform and petroleum ether mixture to yield 5.4 g of the desired compound m.pt. 42°-46° C.

EXAMPLE 5

1-t-Butyl-1-Acetyl-2-Dimethoxyphosphoryl Hydrazine

Acetylchloride (10.8 g) was added dropwise to a stirred solution of triethylamine (13.9 g) and 1-t-butyl-2-dimethoxyphosphoryl hydrazine (9.0 g) in methylenechloride (120 ml) maintained at −20° C. After the addition was complete, the temperature was allowed to rise to 0° C. and kept at this temperature for 1 hour. The mixture was then allowed to warm up to ambient temperature during 2 hours, and the content of the reaction vessel was then stripped to dryness on the rotary evaporator. The residue was extracted with diethylether and the organic extracts dried over magnesium sulfate, filtered and evaporated to dryness, leaving an oil which was subjected to high vacuum for several hours yielding 10.4 g of product.

The following additional compounds given in Table I below were prepared in the manner of the foregoing examples.

Table I

| Example | R | R' | X | Y | Z | M.Pt. (°C.) or $n_D$ | Method of Syn |
|---|---|---|---|---|---|---|---|
| 6 | $(CH_3)_3C-$ | H | O | $-OCH_3$ | $-OC_2H_5$ | — | Ex. 1 |
| 7 | $(CH_3)_3C-$ | H | O | $-OC_2H_5$ | $-OC_2H_5$ | 53°-7° | 1 |
| 8 | $(CH_3)_3C-$ | H | O | $-OC_3H_7^i$ | $-OC_3H_7^i$ | 44°-7° | 1 |
| 9 | $(CH_3)_3C-$ | H | O | $-OC_4H_9^n$ | $-OC_4H_9^n$ | 42°-6° | 1 |
| 10 | $(CH_3)_3C-$ | H | S | $-OC_2H_5$ | $-OC_2H_5$ | 1.4824°-21.5° | 2 |
| 11 | $(CH_3)_3C-$ | H | O | $-OCH_3$ | $-CH_3$ | 110°-12° | 3 |
| 12 | $(CH_3)_3C-$ | H | O | $-OCH_3$ | $-CH_2-CH=CH_2$ | — | 3 |
| 13 | $(CH_3)_3C-$ | H | S | $-CH_3$ | $-CH_3$ | 79°-81° | 3 |
| 14 | $(CH_3)_3C-$ | H | S | $-C_2H_5$ | $-C_2H_5$ | 105°-6° | 3 |
| 15 | $CH_3{\diagdown}CH-{\diagup}C_2H_5$ | H | O | $-OCH_3$ | $-OCH_3$ | 1.4528°-25° | 1 |
| 16 | $CH_3{\diagdown}CH-{\diagup}C_2H_5$ | H | S | $-OCH_3$ | $-OCH_3$ | 1.4916°-24° | 1 |
| 17 | $C_2H_5{\diagdown}C-{\diagup}(CH_3)_2$ | H | O | $-OCH_3$ | $-OCH_3$ | — | 1 |
| 18 | $(CH_3)_3C-$ | H | O | $-OCH_3$ | $-OC_3H_7^n$ | 38°-42° | 3 |

Table I-continued

| Example | R | R' | X | Y | Z | M.Pt. (°C.) or $n_D$ | Method of Syn |
|---------|---|-----|---|---|---|----------------------|---------------|
| 19 | $(CH_3)_3C-$ | $CH_{13}CO-$ | O | $-OC_2H_5$ | $-OC_2H_5$ | 1.4644°-27° | 5 |

EXAMPLE 20

Insecticidal-Miticidal Screening Tests

The compounds of Examples 1–19 were tested as agricultural compositions for insecticidal and miticidal activity against representative species of economically important arthropods, specifically, the Mexican bean beetle, Southern armyworm, the two-spotted spider mite and the black bean aphid, by a combination of soil and foliar application at 250 ppm.

The compositions were tested for primary insecticidal activity against Mexican bean beetle as follows: a combination of stomach poison and feeding deterrent effects was measured on larvae of the Mexican bean beetle about 5 to 7 days after their emerging from eggs. Leaves of young bean plants were removed from the plants by cutting the petioles and were dipped in a suspension of the chemical at 250 ppm in the primary tests. Petioles of the excised leaves were placed in a water reservoir to maintain leaf turgidity and 5 larvae were placed upon them as soon as the chemical deposit was dry. Observations were made on the mortality of the beetles and the extent of inhibition of feeding 2 or 3 days later. The two responses were rated 0 (no effect on mortality or feeding) to 10 (complete destruction of larvae and total inhibition of feeding) against leaves dipped in a commercial standard, namely, Azodrin, which is o,o-dimethyl-o-(2-methyl carbamoyl-1-methylvinyl) phosphate.

The compositions were tested similarly for primary activity at 250 ppm as stomach poisons for 5- to 7-day-old larvae of the Southern armyworm. The larvae were transferred from stock cultures to bean leaves that had been dipped in a suspension of the test composition.

The primary mite contact and systemic tests were carried out on bean plants which were infected with the two-spotted spider mite which 24 hours previously had been dipped in a suspension of the test material at 250 ppm. Immediately afterward 21 ml of a 250 ppm suspension was poured on the surface of the soil at a rate equivalent to 25 lb/acre to provide both contact and systemic effects. Observations were made on adult kill (initial) and immature mite kill (residual). The response in each category was rated on a scale of 0 (ineffective) to 10 (complete destruction). The standard used also was Azodrin applied as a spray at 50, 10 and 2 ppm, or as a soil drench at 2.5, 0.5 and 0.1 lb/acre.

The primary aphid contact and systemic poison tests were made on the black bean aphid while feeding on nasturtium plants. The tests were made on aphids that had migrated to the test plant within the last 24 hours. The foliage and aphids were exposed to a spray of the test chemical at 250 ppm while the plant rotated on a turntable. Immediately thereafter 21 ml of a 520 ppm stock suspension was poured onto the surface of the soil at a rated 25 lb/acre. The plants then were held under fluorescent light for 24 hours and the dead aphids collected. The effectiveness also was rated 0 (no kill) to 10 (complete kill) with Azodrin applied as a spray at 50, 10 and 2 ppm, or as a drench at 2.5, 0.5 and 0.1 lb/acre.

The results of these tests are given in Table II below.

Table II

PRIMARY INSECTICIDE-MITICIDE SCREEN TEST DATA

| Compound of Ex. No. | Mexican Bean Beetle | Southern Armyworm | 2-Spotted Spider Mite Adult | 2-Spotted Spider Mite Immature | Black Bean Aphid |
|---|---|---|---|---|---|
| 1 | 10 | 6 | 10 | 10 | 10 |
| 6 | 10 | 10 | 9 | 8 | 10 |
| 7 | 3 | 0 | 1 | 0 | 6 |
| 8 | 1 | 0 | 10 | 10 | 9 |
| 9 | 8 | 7 | 0 | 0 | 0 |
| 2 | 10 | 4 | 10 | 10 | 10 |
| 10 | 1 | 0 | 6 | 6 | 8 |
| 11 | 10 | 0 | — | — | 10 |
| 12 | 10 | 0 | 10 | 9 | 10 |
| 3 | 8 | 0 | 4 | 2 | 8 |
| 13 | 3 | 0 | 0 | 0 | 1 |
| 14 | 5 | 0 | 0 | 0 | 8 |
| 15 | 0 | 0 | 2 | 2 | 9 |
| 16 | 0 | 0 | 0 | 0 | 9 |
| 5 | 10 | 0 | 9 | 9 | 8 |
| 19 | 3 | 0 | 0 | 0 | 0 |
| 4 | 10 | 9 | 9.5 | 10 | 10 |
| 17 | 10 | 10 | 8 | 8 | 9 |
| 18 | 10 | 7 | 9 | 9 | 9 |
| Standard | 10 | 10 | 10 | 10 | 10 |

Secondary insecticidal-miticidal tests for the compositions of the invention were made as described for the primary tests except that the soil, (systemic) and spray (contact) effect were made on separate plants and in lower dosage levels. Representative test data for Compounds of Examples 1 and 2 are given below in Table III.

Table III

SECONDARY INSECTICIDAL-MITICIDE SCREEN TEST DATA

| Compound of Example No. | Mexican Bean Beetle (kill) | Mexican Bean Beetle (inhib) | 2-S Mite Adult (kill) | 2-S Mite Nymph (kill) | Bean Aphid (kill) |
|---|---|---|---|---|---|
| 1 | | | | | |
| Soil (lb/acre) | | | | | |
| 12.5 | | | 10 | 10 | 9.5 |
| 6.3 | | | 9 | 10 | 8 |
| 3.2 | | | 10 | 20 | 9.5 |
| 1.6 | | | 6 | 6.5 | 9.5 |
| 0.8 | | | 2.5 | 3 | 0.5 |
| Spray (ppm) | | | | | |
| 130 | 10 | 9.5 | 0 | 0 | 9.5 |
| 65 | 10 | 9.5 | 0 | 0 | 9 |
| 33 | 10 | 9.5 | 0 | 0 | 9.5 |
| 16 | 10 | 5.5 | 0.5 | 3 | 9 |
| 8 | 10 | 5.5 | 0 | 0 | 5 |
| 2 | | | | | |
| Soil (lb/acre) | | | | | |
| 12.5 | | | 7 | 0 | 9 |
| 6.3 | | | 1 | 0 | 9 |
| 3.2 | | | 0 | 1 | 9 |
| 3.1 | | | | | 10 |
| 1.5 | | | | | 10 |
| 0.75 | | | | | 10 |
| 0.37 | | | | | 10 |
| Spray (ppm) | | | | | |
| 130 | 7.5 | 7.5 | 1 | 1 | 10 |
| 65 | 4.5 | 4 | 0.5 | 0 | 10 |
| 33 | 0 | 3 | 1 | 0 | 9 |
| 16 | | | | | 7.5 |

Table III-continued
SECONDARY INSECTICIDAL-MITICIDE SCREEN TEST DATA

| Compound of Example No. | Mexican Bean Beetle (kill) | Mexican Bean Beetle (inhib) | 2-S Mite Adult (kill) | 2-S Mite Nymph (kill) | Bean Aphid (kill) |
|---|---|---|---|---|---|
| 8 | | | | | 4 |

Both compounds 1 and 2 are particularly active against bean aphids by either soil or foliar application. The activity by soil application is indicative of a systemic effect whereby the chemical is translocated throughout the plant after root uptake. In addition, compound 1 posessed good contact activity against Mexican bean beetle, and excellent systemic effects against two-spotted mites.

The compositions of the present invention may, if desired, also comprise, in addition to a compound of the present invention, at least one other biologically active ingredient, for example, another insecticide, herbicide or fungicide. They may also comprise a synergist of the type useful in synergising the activity of pyrethroid type insecticides.

While the invention has been described with particular reference to certain embodiments thereof, it will be understood that certain modifications and changes may be made which are within the skill of the art. Therefore it is intended to be bound only by the appended claims.

What is claimed is:

1. Compounds of the formula:

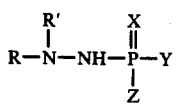

where
R is a secondary or tertiary alkyl, $C_4$-$C_{10}$,
R' is hydrogen, alkyl, $C_1$-$C_6$ or acetyl,
X is oxygen or sulfur, and,
Y and Z are independently alkyl, $C_1$-$C_6$, alkenyl, $C_2$-$C_6$, alkoxy, $C_1$-$C_6$, thioalkoxy, $C_1$-$C_6$.

2. Compounds according to claim 1 in which R is a tertiary alkyl, $C_4$-$C_{10}$.

3. Compounds according to claim 1 in which R' is hydrogen.

4. Compounds according to claim 1 in which R' is alkyl, $C_1$-$C_6$.

5. Compounds according to claim 1 in which R' is acetyl.

6. Compounds according to claim 1 in which X is oxygen.

7. Compounds according to claim 1 in which X is sulfur.

8. Compounds according to claim 1 in which at least one of Y and Z is alkyl, $C_1$-$C_6$.

9. Compounds according to claim 1 in which at least one of Y and Z is alkoxy, $C_1$-$C_6$.

10. Compounds according to claim 1 in which at least one of Y and Z is alkenyl, $C_2$-$C_6$.

11. Compounds according to claim 1 in which both Y and Z are alkoxy, $C_1$-$C_6$.

12. Compounds according to claim 1 in which R is t-butyl.

13. A compound according to claim 1 in which is 1-t-butyl-2-dimethoxyphosphoryl hydrazine.

14. A compound according to claim 1 which is 1-t-butyl-2-dimethoxythiophosphoryl hydrazine.

15. A compound according to claim 1 which is 1-t-butyl-1-methyl-2-dimethoxythiophosphoryl hydrazine.

16. A compound according to claim 1 which is 1-t-butyl-1-acetyl-2-dimethoxyphosphoryl hydrazine.

17. A composition for combatting insect or mite pests at a locus which comprises an insecticidally or miticidally effective amount of a compound according to claim 1 and an acceptable diluent or carrier material.

18. A method of combatting insect or mite pests at a locus which comprises treating the locus with an insecticidally or miticidally effective amount of a composition according to claim 17.

* * * * *